United States Patent
Waite et al.

(10) Patent No.: US 12,220,493 B2
(45) Date of Patent: Feb. 11, 2025

(54) NITRIC OXIDE PRODUCING COLLAGEN/ORC DRESSING

(71) Applicant: SYSTAGENIX WOUND MANAGEMENT, LIMITED, West Sussex (GB)

(72) Inventors: Alexander Waite, West Sussex (GB); Carrina Ward, West Sussex (GB)

(73) Assignee: Systagenix Wound Management, Limited, West Sussex (GB)

( * ) Notice: Subject to any disclaimer, the term of this patent is extended or adjusted under 35 U.S.C. 154(b) by 1024 days.

(21) Appl. No.: 17/259,650

(22) PCT Filed: Jul. 15, 2019

(86) PCT No.: PCT/IB2019/056038
§ 371 (c)(1),
(2) Date: Jan. 12, 2021

(87) PCT Pub. No.: WO2020/016758
PCT Pub. Date: Jan. 23, 2020

(65) Prior Publication Data
US 2021/0330855 A1     Oct. 28, 2021

Related U.S. Application Data

(60) Provisional application No. 62/698,552, filed on Jul. 16, 2018.

(51) Int. Cl.
*A61L 15/44* (2006.01)
*A61L 15/22* (2006.01)
*A61L 15/64* (2006.01)

(52) U.S. Cl.
CPC ............. *A61L 15/44* (2013.01); *A61L 15/225* (2013.01); *A61L 15/64* (2013.01);
(Continued)

(58) Field of Classification Search
CPC ....................................................... A61L 15/44
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, Md and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Benjamin J Packard

(57) ABSTRACT

The present disclosure provides wound dressing compositions that stimulate nitric oxide production in a wound upon application. The wound dressing composition includes a first layer comprising collagen and an oxidized cellulose and a second layer comprising a nitrite source. Also disclosed herein are kits comprising the wound dressing compositions of the present technology.

19 Claims, 2 Drawing Sheets

| Bacterial Species | Layer 2 (n=3) | Layer 1 (n=3) | Bilayer Dressing (n=3) |
|---|---|---|---|
| *P. aeruginosa* | Full bacterial growth | 0 mm | 2.3 mm |
| *S. aureus* | Full bacterial growth | 0.2 mm | 1.5 mm |

(52) U.S. Cl.
CPC .... *A61L 2300/114* (2013.01); *A61L 2300/404* (2013.01); *A61L 2300/412* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2016/0089473 A1 | 3/2016 | Wood et al. |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 1 795 210 A2 | 6/2007 | |
| EP | 2781224 A1 * | 9/2014 | ............ A61K 35/16 |
| EP | 3 338 813 A1 | 6/2018 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998,

(56) References Cited

OTHER PUBLICATIONS vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Dave et al., "Biomedical evaluation of a novel nitrogen oxides releasing wound dressing," J Mater Sci Mater Med. 2012, vol. 23, No. 12, p. 3097-3106.
International Search Report and Written Opinion in International Application No. PCT/IB2019/056038, mailed on Dec. 17, 2019.
Zhu et al., "Nitric oxide accelerates the recovery from burn wounds," World J Surg. 2007, vol. 31, No. 4, p. 624-631.

\* cited by examiner

Figure 1

| Bacterial Species | Layer 2 (n=3) | Layer 1 (n=3) | Bilayer Dressing (n=3) |
|---|---|---|---|
| *P. aeruginosa* | Full bacterial growth | 0 mm | 2.3 mm |
| *S. aureus* | Full bacterial growth | 0.2 mm | 1.5 mm |

NITRIC OXIDE PRODUCING COLLAGEN/ORC DRESSING

CROSS-REFERENCE TO RELATED PATENT APPLICATIONS

This application is a US National Stage Application under 35 U.S.C. § 371 of International Application No. PCT/IB2019/056038, filed on Jul. 15, 2019, which claims the benefit of and priority to U.S. Provisional Appl. No. 62/698,552, filed Jul. 16, 2018, the disclosure of each of which is incorporated by reference herein in its entirety.

TECHNICAL FIELD

The present technology relates generally to wound dressing compositions including a first layer comprising collagen and/or an oxidized regenerated cellulose (ORC) and a second layer comprising a nitrite source, and the uses thereof. Kits for use in practicing the methods are also provided.

BACKGROUND

The following description of the background of the present technology is provided simply as an aid in understanding the present technology and is not admitted to describe or constitute prior art to the present technology.

A wide variety of materials and devices, generally characterized as "dressings," are known in the art for use in treating an injury or other tissue disruptions. Such wounds may be the result of trauma, surgery, or disease, and may affect skin or other tissues. Dressings may control bleeding, absorb wound exudate, ease pain, assist in debriding the wound, protect wound tissue from infection, or otherwise promote healing and protect the wound from further damage.

Infections can retard wound healing and, if untreated, can result in tissue loss, systemic infections, septic shock, and death. Thus, there is an urgent need for wound dressing compositions that protect wound tissue from infection.

SUMMARY OF THE PRESENT TECHNOLOGY

In one aspect, the present disclosure provides a wound dressing composition comprising a first layer and a second layer, wherein the first layer comprises a collagen and an oxidized cellulose, and wherein the second layer comprises a nitrite source. In some embodiments of the wound dressing composition, the first layer comprises about 30 wt. % to about 95 wt. % of collagen, with a weight-average molecular weight of about 5,000 to about 100,000; about 30 wt. % to about 70 wt. % of oxidized cellulose, with a weight-average molecular weight of about 50,000 to about 1,000,000. In certain embodiments of the wound dressing composition, the second layer comprises about 10 wt. % to about 90 wt. % of the nitrite source.

Additionally or alternatively, in some embodiments, the collagen is selected from the group consisting of a mammalian collagen, a marine collagen, a porcine collagen, an ovine collagen, an equine collagen, and any combination thereof. Additionally or alternatively, in some embodiments, the collagen is a mammalian collagen. Additionally or alternatively, in some embodiments, the collagen is a human recombinant collagen. Additionally or alternatively, in some embodiments, the collagen is a human recombinant collagen, wherein the human recombinant collagen is a mixture of type I human recombinant collagen and type III human recombinant collagen. Examples of the type I human recombinant collagen include human recombinant collagen type I, alpha I or human recombinant collagen type I, alpha II. Examples of the the type III human recombinant collagen include human recombinant collagen type III, alpha I. Additionally or alternatively, in some embodiments, the ratio by weight of type I human recombinant collagen to type III human recombinant collagen is greater than 70:30.

Additionally or alternatively, in some embodiments, the collagen is a bovine collagen. Additionally or alternatively, in some embodiments, the collagen is a bovine collagen, wherein the bovine collagen is a mixture of type I bovine collagen and type III bovine collagen. Additionally or alternatively, in some embodiments, the ratio by weight of type I bovine collagen to type III bovine collagen is about 85:15.

Additionally or alternatively, in some embodiments, the oxidized cellulose comprises oxidized regenerated cellulose (ORC).

Additionally or alternatively, in some embodiments, the oxidized cellulose of the first layer may comprise a weight-average molecular weight of about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of these values.

Additionally or alternatively, in some embodiments, the oxidized cellulose of the first layer comprises fiber lengths of about 5 µm to about 1,000 µm. Additionally or alternatively, in some embodiments, the ORC of the first layer may comprise fibers lengths of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 220 µm, about 230 µm, about 240 µm, about 250 µm, about 260 µm, about 280 µm, about 300

μm, about 320 μm, about 340 μm, about 360 μm, about 380 μm, about 400 μm, about 420 μm, about 440 μm, about 460 μm, about 480 μm, about 500 μm, about 550 μm, about 600 μm, about 650 μm, about 700 μm, about 750 μm, about 800 μm, about 850 μm, about 900 μm, about 950 μm, about 1,000 μm, or any range including and/or in between any two of these values.

Additionally or alternatively, in some embodiments, the first layer comprises a freeze dried sponge or a film.

Additionally or alternatively, in some embodiments, the wound dressing composition is a single multi-layered dressing, wherein the first layer and the second layer are adjoined.

Additionally or alternatively, in some embodiments, the first layer of the wound dressing composition comprises one or more additional biomaterials. Examples of the one or more additional biomaterials include gelatin, chitosan, fibronectin, hyaluronic acid, polysaccharides, or any combination thereof.

Additionally or alternatively, in some embodiments, the first layer of the wound dressing composition comprises at least one antimicrobial agent. Examples of the at least one antimicrobial agent include tetracycline, penicillins, terramycins, erythromycin, bacitracin, neomycin, polymycin B, mupirocin, clindamycin, colloidal silver, silver salts, silver sulfadiazine, chlorhexidine, povidone iodine, triclosan, sucralfate, quaternary ammonium salts, or any combination thereof.

Additionally or alternatively, in some embodiments, the first layer of the wound dressing composition comprises at least one antioxidant. Examples of the at least one antioxidant include anthocyanins, astaxanthin, bilirubin, canthaxanthin, capsaicin, citric acid, curcumin, coenzyme Q10, eugenol, flavanol, flavonolignans, flavanone, flavone, flavonol, iodide, isoflavone phytoestrogen, lutein, lycopene, manganese, melatonin, N-acetylcysteine, oxalic acid, phenolic acid, phytic acid, R-α-lipoic acid, stilbenoid, tocopherol, tocotrienol, vitamin A, vitamin C, vitamin E, xanthones, zeaxanthin, α-carotene, β-carotene, or any combination thereof.

Additionally or alternatively, in some embodiments, the first layer of the wound dressing composition comprises at least one signaling protein. Examples of the at least one signaling protein include PDGF, TGFβ, FGF, EGF, or any combination thereof.

Additionally or alternatively, in some embodiments, the second layer of the wound dressing composition comprises a nitrite source selected from the group consisting of aluminum nitrite, ammonium nitrite, barium nitrite, beryllium nitrite, cadmium nitrite, calcium nitrite, chromium (II) nitrite, chromium (III) nitrite, cobalt (II) nitrite, cobalt (III) nitrite, copper (I) nitrite, copper (II) nitrite, gallium (III) nitrite, iron (II) nitrite, iron (III) nitrite, lead (II) nitrite, lead (IV) nitrite, lithium nitrite, magnesium nitrite, manganese (II) nitrite, mercury (I) nitrite, nickel (II) nitrite, nickel (III) nitrite, potassium nitrite, rubidium nitrite, silver nitrite, sodium nitrite, strontium nitrite, tin (II) nitrite, tin (IV) nitrite, zinc nitrite, and any combination thereof.

Additionally or alternatively, in some embodiments, the second layer comprises about 1 wt. % to about 90 wt. % of the nitrite source. Additionally or alternatively, in some embodiments, the second layer comprises about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 12 wt. %, about 14 wt. %, about 16 wt. %, about 18 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of these values.

Additionally or alternatively, in some embodiments, the second layer comprises a bioresorbable layer. Additionally or alternatively, in some embodiments, the bioresorbable layer is selected from the group consisting of collagen, gelatin, chitosan, fibronectin, hyaluronic acid, polysaccharides, and any combination thereof. Additionally or alternatively, in some embodiments, the bioresorbable layer comprises about 5 wt. % to about 100 wt. % of the second layer, or about about 10 wt. % to about 90 wt. % of the second layer.

Additionally or alternatively, in some embodiments, the second layer comprises a non-bioresorbable layer. Additionally or alternatively, in some embodiments, the non-bioresorbable layer is selected from the group consisting of a coating, a gel, a liquid, and any combination thereof. Additionally or alternatively, in some embodiments, the non-bioresorbable layer comprises about 10 wt. % to about 99 wt. % of the second layer.

Additionally or alternatively, in some embodiments, the first layer and the second layer are adjoined. Additionally or alternatively, in some embodiments, the first layer and the second layer are not adjoined.

Additionally or alternatively, in some embodiments, the wound dressing composition induces, enhances, or promotes at least of one angiogenesis, vasodilation, or immune response in the subject.

Additionally or alternatively, in some embodiments, the wound dressing composition is bioresorbable and is administered directly to the wound. Additionally or alternatively, in some embodiments, the wound dressing composition is non-bioresorbable and is administered directly to the wound.

In another aspect, the present disclosure provides a method for treating a wound in a subject in need thereof comprising administering to the wound a wound dressing composition comprising a first layer and a second layer, wherein the first layer comprises an effective amount of collagen and an oxidized cellulose, and wherein the second layer comprises an effective amount of a nitrite source. The wound may be a chronic wound or an acute wound.

In another aspect, the present disclosure provides a method for protecting a wound from infection in a subject in need thereof comprising administering to the wound a wound dressing composition comprising a first layer and a second layer, wherein the first layer comprises an effective amount of collagen and an oxidized cellulose, and wherein the second layer comprises an effective amount of a nitrite source. The wound may be a chronic wound or an acute wound.

In another aspect, the present disclosure provides a method for making a wound dressing composition comprising, providing a first layer comprising an effective amount of a collagen and an oxidized cellulose, providing a second layer comprising an effective amount of a nitrite source, and combining the first layer and the second layer to form the wound dressing.

Also provided herein are kits comprising the wound dressing compositions of any embodiment described herein and instructions for use.

BRIEF DESCRIPTION OF THE DRAWINGS

FIG. 1 shows the results of a zone of inhibition assay utilized to assess antimicrobial effect as a measure of nitric oxide production of the bilayer dressing sample, the first layer alone, or the second layer alone.

DETAILED DESCRIPTION

Figure 2:
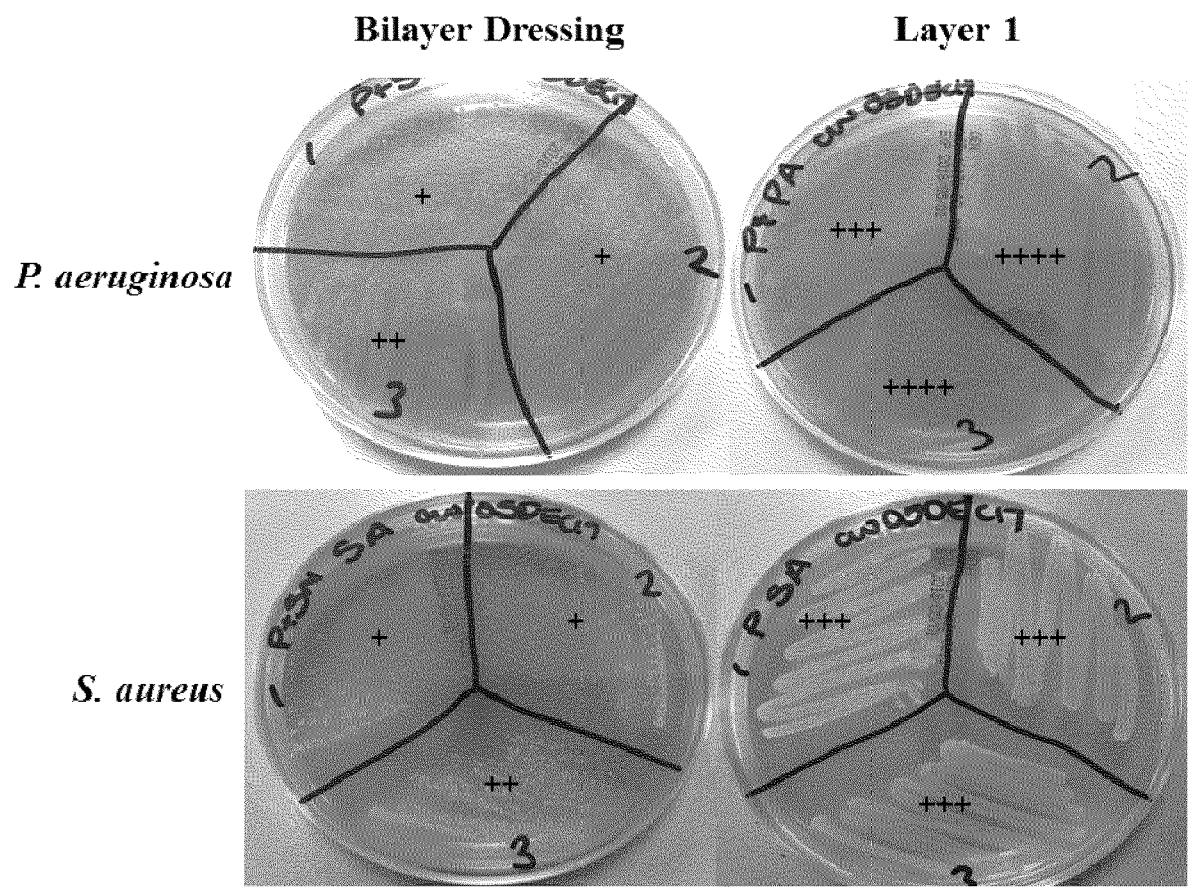
FIG. 2 shows a swab analysis of the area under the bilayer dressing sample and the first layer alone.

It is to be appreciated that certain aspects, modes, embodiments, variations and features of the present methods are described below in various levels of detail in order to provide a substantial understanding of the present technology.

Wounds are typically contaminated by bacteria, however when the immune system cannot cope with normal bacterial growth, a wound can become infected. An infected wound is a wound in which bacteria or other microorganisms have colonized, causing a deterioration and delay in the healing of the wound.

The present disclosure provides wound dressing compositions that stimulate nitric oxide production in a wound upon application. Nitric oxide is a signaling molecule vital to key processes in wound healing such as angiogenesis, vasodilation, and immune response. Example 1 of the present disclosure demonstrates that a single layer comprising only the nitrite source is ineffective in inhibiting bacterial infection. In contrast, the wound dressing composition of the present technology are useful for treating infected wounds and/or protecting wounds from bacterial infection.

Definitions

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "homogeneous" will be understood by persons of ordinary skill in the art to refer to a solid, a liquid, or a gas mixture that has uniform proportions and/or distributions of its components throughout any given sample.

As used herein, the term "solid content" refers to the density of a layer of the wound dressing composition of the present technology, which is its mass per unit volume.

As used herein, the term "saturated" and/or "saturated solution" refers to a solution that has reached the point of maximum concentration, in which no more solute may be dissolved in the solvent.

As used herein, the term "solute" refers to is defined as the substance that is dissolved in a solution.

As used herein, the term "solvent" refers to the component of a solution that is present in the greatest amount. It is the substance in which the solute is dissolved.

The term "mammalian recombinant collagen" refers to collagen manufactured by culturing a non-human organism or mammalian or non-mammalian cells to express at least one exogenous gene encoding a collagen in the culturing system. The term "human recombinant collagen" refers to collagen manufactured by culturing a non-human organism or mammalian or non-mammalian cells to express at least one human gene encoding a collagen. The human recombinant collagen may be selected from the group consisting of collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XXIV, type XXV, type XXVI, and type XXVII. The human recombinant collagen can be collagen of one type free of any other type, or can be a mixture of collagen types. Suitably, the collagen comprises collagens selected from the group consisting of collagen type I, collagen type III, and mixtures thereof. The term "bovine recombinant collagen" refers to collagen manufactured by culturing a non-human organism or mammalian or non-mammalian cells to express at least one bovine gene encoding a collagen. The bovine recombinant collagen may be selected from the group consisting of collagen type I, type II, type III, and type IV. The bovine recombinant collagen can be collagen of one type free of any other type, or can be a mixture of collagen types. Suitably, the collagen comprises collagens selected from the group consisting of collagen type I, collagen type III, and mixtures thereof.

As understood by one of ordinary skill in the art, "molecular weight" (also known as "relative molar mass") is a dimensionless quantity but is converted to molar mass by multiplying by 1 gram/mole—for example, collagen with a weight-average molecular weight of 5,000 has a weight-average molar mass of 5,000 g/mol.

As used herein, the "administration" of a wound dressing composition to a subject includes any route of introducing or delivering to a subject a wound dressing composition to perform its intended function. Administration can be carried out by any suitable route, including but not limited to, topical administration. Administration includes self-administration and the administration by another.

As used herein, the term "effective amount" refers to a quantity sufficient to achieve a desired therapeutic and/or prophylactic effect, e.g., an amount which results in the decrease in a wound described herein or one or more signs or symptoms associated with a wound described herein. In the context of therapeutic or prophylactic applications, the amount of a composition administered to the subject will vary depending on the composition, the degree, type, and severity of the wound and on the characteristics of the individual. The compositions can also be administered in combination with one or more additional therapeutic compounds. In the methods described herein, the therapeutic compositions may be administered to a subject having one or more wounds.

As used herein, the terms "individual", "patient", or "subject" can be an individual organism, a vertebrate, a mammal, or a human. In some embodiments, the individual, patient or subject is a human.

"Treating" or "treatment" as used herein covers the treatment of a wound described herein, in a subject, such as a human, and includes: (i) inhibiting a wound, i.e., arresting its development; (ii) relieving a wound, i.e., causing regression of the wound; (iii) slowing progression of the wound; and/or (iv) inhibiting, relieving, or slowing progression of one or more symptoms of the wound. In some embodiments, treatment means that the symptoms associated with the wound are, e.g., alleviated, reduced, cured, or placed in a state of remission.

It is also to be appreciated that the various modes of treatment of wounds as described herein are intended to mean "substantial," which includes total but also less than total treatment, and wherein some biologically or medically relevant result is achieved. The treatment may be a continuous prolonged treatment for a chronic wound or a single, or few time administrations for the treatment of an acute wound.

The Wound Dressing of the Present Technology

The First Layer

The present disclosure provides a wound dressing composition comprising a first layer wherein the first layer comprises a collagen and an oxidized cellulose. Without wishing to be bound by theory, it is believed that the first layer provides a sustained pH lowering effect (generation of H+ ions) which supports the generation of nitric oxide from a second layer. While the first layer showed poor antimicrobial activity (FIG. 1), the wound dressing composition of the present technology exhibited greater antimicrobial effect compared to the first layer alone, and that the wound dressing composition disclosed herein is effective in promoting nitric oxide production.

In any embodiment disclosed herein, the collagen of the first layer may be selected from the group consisting of a mammalian collagen, a marine collagen, a porcine collagen, an ovine collagen, an equine collagen, and any combination thereof.

In any embodiment disclosed herein, the collagen of the first layer may comprise mammalian collagen. Additionally or alternatively, in some embodiments, the collagen of the first layer may comprise human collagen type I and human collagen type III. Additionally or alternatively, in some embodiments, the collagen of the first layer may comprise bovine collagen type I and bovine collagen type III.

In any embodiment disclosed herein, mammalian recombinant collagen of the first layer may be provided by any suitable method known in the art. Additionally or alternatively, in some embodiments, human recombinant collagen of the first layer may be provided by any suitable method known in the art. For example, the step of providing human recombinant collagen may comprise following the protocol described in U.S. Pat. No. 5,962,648, the entire content of which is incorporated herein by reference. Further recombinant processes are set forth in U.S. Pat. No. 5,593,859 and WO2004/078120, which are also incorporated herein by reference. Additionally or alternatively, in some embodiments, collagen will be recombinantly manufactured by culturing a cell which has been transfected with at least one gene encoding the polypeptide comprising collagen and genes encoding the oxidized cellulose and subunits of the post-translational enzyme prolyl 4-hydroxylase and purifying the resultant collagen monomer therefrom. The human recombinant collagen solution may be subsequently subjected to polymerization or cross-linking conditions to produce an insoluble fibrous collagen.

In any embodiment disclosed herein, the collagen of the first layer may comprise about 30 wt. % to about 95 wt. %, with a weight-average molecular weight of about 5,000 to about 100,000. Additionally or alternatively, in some embodiments, the amount of collagen in the first layer may be about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 95 wt. %, or any range including and/or in between any two of these values. Additionally or alternatively, in some embodiments, the collagen of the first layer comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 45,000, about 50,000, about 55,000, about 60,000, about 65,000, about 70,000, about 75,000, about 80,000, about 85,000, about 90,000, about 95,000, about 100,000, or any range including and/or in between any two of these values.

In any embodiment disclosed herein, the collagen of the first layer may comprise a weight ratio of human collagen type I to human collagen type III of about 100:0, about 90:10, about 80:20, about 70:30, about 60:40, about 50:50, about 40:60, about 30:70, about 20:80, about 10:90, about 0:100, or any range including and/or in between any two of these values. Additionally or alternatively, in some embodiments, the ratio by weight of human collagen type I to human collagen type III is greater than about 50:50, or greater than about 70:30. Additionally or alternatively, in some embodiments, the collagen of the first layer may comprise a weight ratio of type I bovine collagen to type III bovine collagen of about 85:15.

In any embodiment disclosed herein, oxidized regenerated cellulose (ORC) may be produced by the oxidation of cellulose, for example with dinitrogen tetroxide and/or as described in U.S. Pat. No. 3,122,479 (incorporated herein by reference). Without wishing to be bound by theory, it is believed that this process may convert primary alcohol groups on the saccharide residues of the celluolse to carboxylic acid groups, for example, forming uronic acid residues within the cellulose chain. The oxidation may not proceed with complete selectivity, and as a result hydroxyl groups on carbons 2 and 3 of the saccharide residue may be converted to the keto form. These ketone units may introduce an alkali labile link, which at pH 7 or higher initiates the decomposition of the polymer via formation of a lactone and sugar ring cleavage. As a result, oxidized regenerated cellulose is biodegradable and bioresorbable under physiological conditions. ORC is available with a variety of degrees of oxidation and hence rates of degradation.

In any embodiment disclosed herein, the ORC of the first layer may comprise about 30 wt. % to about 70 wt. %, with a weight-average molecular weight of about 50,000 to about 1,000,000. Additionally or alternatively, in some embodiments, the ORC in the first layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of these values. Additionally or alternatively, in some embodiments, the ORC of the first layer may comprise a weight-average molecular weight of about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of these values.

The ORC may include particles, fibers, or both; in any embodiment disclosed herein, the ORC may be in the form of particles, such as fiber particles or powder particles. In embodiments that include ORC fibers, the ORC fibers may have a volume fraction such that at least 80% of the fibers have lengths in the range from about 5 μm to about 1,000 μm. Additionally or alternatively, in some embodiments, the ORC of the first layer may comprise fibers lengths of about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 55 μm, about 60 μm, about 65 μm, about 70 μm, about 75 μm, about 80 μm, about 85 μm, about 90 μm, about 95 μm, about 100 μm, about 110 μm, about 120 μm, about 130 μm, about 140 μm, about 150 μm, about 160 μm, about 170 μm, about 180 μm, about 190 μm, about 200 μm, about 220 μm, about 230 μm, about 240 μm, about 250 μm, about 260 μm, about 280 μm, about 300 μm, about 320 μm, about 340 μm, about 360 μm, about 380 μm, about 400 μm, about 420 μm, about 440 μm, about 460 μm, about 480 μm, about 500 μm, about 550 μm, about 600 μm, about 650 μm, about 700 μm, about 750 μm, about 800 μm, about 850 μm, about 900 μm, about 950 μm, about 1,000 μm, or any range including and/or in between any two of these values.

In any embodiment disclosed herein, the mixture of collagen and ORC within the first layer of the present technology may comprise about 30 wt. % to about 90 wt. %. Additionally or alternatively, in some embodiments, the collagen and ORC mixture of the first layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of these values.

In any embodiment disclosed herein, the first layer may comprise about 1 wt. % to about 60 wt. % of one or more additional biomaterials. Additionally or alternatively, in some embodiments, the one or more additional biomaterials of the first layer may comprise about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, or any range including and/or in between any two of these values. Additionally or alternatively, in some embodiments, the one or more additional biomaterials included in the first layer may be selected from the group consisting of gelatin, chitosan, fibronectin, hyaluronic acid, polysaccharides, and any combination thereof.

In any embodiment disclosed herein, the first layer may comprise about 0.001 wt. % to about 15 wt. % of at least one antimicrobial agent. Additionally or alternatively, in some embodiments, the at least one antimicrobial agent may comprise about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, or any range including and/or in between any two of these values. Additionally or alternatively, in some embodiments, the at least one antimicrobial agent is selected from the group consisting of tetracycline, penicillins, terramycins, erythromycin, bacitracin, neomycin, polymycin B, mupirocin, clindamycin, colloidal silver, silver salts, silver sulfadiazine, chlorhexidine, povidone iodine, triclosan, sucralfate, quaternary ammonium salts, and any combination thereof.

In any embodiment disclosed herein, the first layer may comprise about 0.001 wt. % to about 15 wt. % of at least one antioxidant. Additionally or alternatively, in some embodiments, the at least one antioxidant may comprise about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, or any range including and/or in between any two of these values. Additionally or alternatively, in some embodiments, the first layer disclosed herein may comprise at least one antioxidant selected from the group consisting of anthocyanins, astaxanthin, bilirubin, canthaxanthin, capsaicin, citric acid, curcumin, coenzyme Q10, eugenol, flavanol, flavonolignans, flavanone, flavone, flavonol, iodide, isoflavone phytoestrogen, lutein, lycopene, manganese, melatonin, N-acetylcysteine, oxalic acid, phenolic acid, phytic acid, R-α-lipoic acid, stilbenoid, tocopherol, tocotrienol, vitamin A, vitamin C, vitamin E, xanthones, zeaxanthin, α-carotene, β-carotene, and any combination thereof.

Examples of anthocyanins include, but are not limited to cyanidin, delphinidin, malvidin, pelargonidin, peonidin, petunidin, and mixtures thereof.

Examples of flavanols include, but are not limited to catechin, epicatechin, theaflavin, thearubigins, gallocatechin, epigallocatechin, or any gallate ester thereof, and mixtures thereof.

Examples of flavanones include, but are not limited to eriodictyol, hesperetin, naringenin, and mixtures thereof.

Examples of flavones include, but are not limited to apigenin, luteolin, tangeritin, and mixtures thereof.

Examples of flavonols include, but are not limited to isorhamnetin, kaempferol, myricetin, proanthocyanidins, quercetin, rutin, and mixtures thereof.

Examples of isoflavone phytoestrogens include, but are not limited to daidzein, genistein, glycitein, and mixtures thereof.

Examples of phenolic acids include, but are not limited to chicoric acid, chlorogenic acid, cinnamic acid, ellagic acid, ellagitannins, gallic acid, gallotannins, rosmarinic acid, salicylic acid, or any ester thereof, and mixtures thereof.

Examples of stillbenoids include, but are not limited to resveratrol, pterostilbene, and mixtures thereof.

In any embodiment disclosed herein, the first layer may comprise about 0.001 wt. % to about 5 wt. % of at least one signaling protein. Additionally or alternatively, in some embodiments, the at least one signaling protein may comprise about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, or any range including and/or in between any two of these values. Additionally or alternatively, in some embodiments, the first layer disclosed herein may comprise at least one signaling protein selected from the group consisting of PDGF, TGFβ, FGF, EGF, and any combination thereof.

The Second Layer

The present disclosure provides a wound dressing composition comprising a second layer wherein the second layer comprises a nitrite source. Nitric oxide is a signaling molecule vital to wound healing with a pivotal role in angiogenesis, vasoldilation, and immune response (i.e. increased blow flow to the wound site and antimicrobial effects).

In any embodiment disclosed herein, the nitrite source of the second layer may comprise about 1 wt. % to about 90 wt. %. Additionally or alternatively, in some embodiments, the amount of the nitrite source in the second layer may be about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 12 wt. %, about 14 wt. %, about 16 wt. %, about 18 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of these values. Additionally or alternatively, in some embodiments, the nitrite source of the second layer disclosed herein may be selected from the group consisting of aluminum nitrite, ammonium nitrite, barium nitrite, beryllium nitrite, cadmium nitrite, calcium nitrite, chromium (II) nitrite, chromium (III) nitrite, cobalt (II) nitrite, cobalt (III) nitrite, copper (I) nitrite, copper (II) nitrite, gallium (III) nitrite, iron (II) nitrite, iron (III) nitrite, lead (II) nitrite, lead (IV) nitrite, lithium nitrite, magnesium nitrite, manganese (II) nitrite, mercury (I) nitrite, nickel (II) nitrite, nickel (III) nitrite, potassium nitrite, rubidium nitrite, silver nitrite, sodium nitrite, strontium nitrite, tin (II) nitrite, tin (IV) nitrite, zinc nitrite, and any combination thereof.

In some embodiments, the second layer may comprise a material selected from the group consisting of gauze, cotton, rayon, polyester, collagen, gelatin, chitosan, fibronectin, hyaluronic acid, polysaccharides, a coating, a gel, a liquid, and any combination thereof. Additionally or alternatively, in some embodiments, the material of the second layer may be saturated in any nitrite source disclosed herein. In some embodiments, the saturated material of the second layer is a gauze.

The Wound Dressing Composition

The present disclosure provides a wound dressing composition comprising the first layer and the second layer disclosed herein.

In any embodiment disclosed herein, the second layer comprising the nitrite source may comprise a bioresorbable layer. Additionally or alternatively, in some embodiments, the bioresorbable layer may comprise about 5 wt. % to about 100 wt. % of the second layer. Additionally or alternatively, in some embodiments, the bioresorbable layer may comprise about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 96 wt. %, about 98 wt. %, about 100 wt. %, or any range including and/or in between any two of these values. Additionally or alternatively, in some embodiments, the bioresorbable second layer is composed of collagen, gelatin, chitosan, fibronectin, hyaluronic acid, polysaccharides, or any combination thereof.

In any embodiment disclosed herein, the second layer comprising the nitrite source may comprise a non-bioresorbable layer. Additionally or alternatively, in some embodiments, the non-bioresorbable layer may comprise about 10 wt. % to about 99 wt. % of the second layer. Additionally or alternatively, in some embodiments, the non-bioresorbable layer may comprise about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 96 wt. %, about 98 wt. %, about 99 wt. %, or any range including and/or in between any two of these values. Additionally or alternatively, in some embodiments, the non-bioresorbable second layer is a coating, a gel, a liquid, or any combination thereof.

In any embodiment disclosed herein, the wound dressing composition comprises the first layer and the second layer wherein the first layer and the second layer are adjoined. Additionally or alternatively, in some embodiments, the first layer may be in the form of a freeze dried sponge or a film material. Additionally or alternatively, in some embodiments, the second layer may be in the form of a freeze dried sponge or a film material. In any embodiment disclosed herein, a suitable sponge is made by freeze drying or solvent drying an aqueous dispersion consisting essentially of mammalian recombinant collagen particles or fibers and ORC fibers, together with suitable therapeutic agents. Additionally or alternatively, in some embodiments, the wound dressing compositions of the present technology are freeze dried sponges of human recombinant collagen and ORC substantially as described in EP-A-1153622, the entire content of which is incorporated herein by reference. Additionally or alternatively, in some embodiments, the second layer may comprise a film a coating, a gel, a liquid, or any combination thereof.

In any embodiment disclosed herein, the wound dressing composition comprises the first layer and the second layer, wherein the first layer and the second layer are not adjoined. Additionally or alternatively, in some embodiments, the wound dressing composition may be in the form of a freeze dried sponge or a film material. In any embodiment disclosed herein, a suitable sponge is made by freeze drying or solvent drying an aqueous dispersion consisting essentially of mammalian recombinant collagen particles or fibers and ORC fibers, together with suitable therapeutic agents. Additionally or alternatively, in some embodiments, the wound dressing composition of the present technology are freeze dried sponges of human recombinant collagen and ORC substantially as described in EP-A-1153622 (supra). Additionally or alternatively, in some embodiments, the second layer may comprise a film a coating, a gel, a liquid, or any combination thereof.

In any embodiment disclosed herein, the average pore size of the freeze dried sponge is about 10-500 µm, or about 100-300 µm. Additionally or alternatively, in some embodiments, the average pore size of the freeze dried sponge is about 10 µm, about 12 µm, about 14 µm, about 16 µm, about 18 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 220 µm, about 240 µm, about 260 µm, about 280 µm, about 300 µm, or any range including and/or in between any two of these values.

In some embodiments, the second layer may comprise a material selected from the group consisting of gauze, cotton, rayon, polyester, collagen, gelatin, chitosan, fibronectin, hyaluronic acid, polysaccharides, a coating, a gel, a liquid, and any combination thereof. Additionally or alternatively, in some embodiments, the material of the second layer may be saturated in any nitrite source disclosed herein. In some embodiments, the saturated material of the second layer is a gauze.

In some embodiments, the wound dressing composition of the present disclosure is sterile and packaged in a microorganism-impermeable container.

Therapeutic and Prophylactic Methods of the Present Technology

In one aspect, the present disclosure provides a method of treating a wound in a subject in need thereof, wherein the method comprises administering to the wound a wound dressing composition of any embodiment described herein. In some embodiments, the wound may be an acute wound or a chronic wound. Additionally or alternatively, in some embodiments, the wound is an acute wound selected from the group consisting of surgical wounds, trauma wounds, donor sites, graft sites, and burn wounds. Additionally or alternatively, in some embodiments, the wound is a chronic wound selected from the group consisting of infectious wounds, venous ulcers, decubitis ulcers and diabetic ulcers. In some embodiments, the wound dressing protects the wound from infection. The infection may be a bacterial infection or a fungal infection. In some embodiments, the bacterial infection is caused by gram-negative or gram-positive bacteria.

Examples of gram-positive bacteria include, but are not limited to *Actinomyces* sp., *Arcanobacterium* sp., *Bacillus* sp., *Bavariicoccus* sp., *Brachybacterium* sp., *Clostridium* sp., *Cnuibacter* sp., *Corynebacterium* sp., *Enterococcus* sp., *Desulfitobacterium* sp., *Fervidobacterium* sp., *Georgenia* sp., *Janibacter* sp., *Lactobacillales* sp., *Microbispora* sp., *Nocardia* sp., *Pasteuria* sp., *Pilibacter* sp., *Propionibacterium* sp., *Rathayibacter* sp., *Rhodococcus* sp., *Roseburia* sp., *Rothia* sp., *Sarcina* sp., *Solibacillus* sp., *Sporosarcina* sp., *Staphylococcus* sp., *Streptococcus* sp., *Syntrophomonas* sp., or *Tepidibacter* sp.

Examples of gram-negative bacteria include, but are not limited to *Acetobacter* sp., *Acidaminococcus* sp., *Acinetobacter* sp., *Agrobacterium* sp., *Akkermansia* sp., *Anaerobiospirillum* sp., *Anaerolinea* sp., *Arcobacter* sp., *Armatimonas* sp., *Azotobacter* sp., *Bacteroides* sp., *Bacteroidetes* sp., *Bartonella* sp., *Bdellovibrio* sp., *Brachyspira* sp., *Bradyrhizobium* sp., *Caldilinea* sp., *Cardiobacterium* sp., *Christensenella* sp., *Chthonomonas* sp., *Coxiella* sp., *Cyanobacteria* sp., *Cytophaga* sp., *Dehalogenimonas* sp., *Desulfurobacterium* sp., *Devosia* sp., *Dialister* sp., *Dictyoglomus* sp., *Dinoroseobacter* sp., *Enterobacter* sp., *Escherichia* sp., *Fimbriimonas* sp., *Flavobacterium* sp., *Francisella* sp., *Fusobacterium* sp., *Gluconacetobacter* sp., *Haemophilus* sp., *Helicobacter* sp., *Kingella* sp., *Klebsiella* sp., *Kluyvera* sp., *Kozakia* sp., *Legionella* sp. *Leptonema* sp. *Leptotrichia* sp., *Levilinea* sp. *Luteimonas* sp. *Megamonas* sp., *Megasphaera* sp., *Meiothermus* sp., *Methylobacterium* sp., *Moraxella* sp., *Morganella* sp., *Mycoplasma* sp., *Neisseria* sp., *Nitrosomonas* sp., *Pectinatus* sp., *Pedobacter* sp., *Pelosinus* sp., *Propionispora* sp., *Proteus* sp., *Pseudomonas* sp., *Pseudoxanthomonas* sp., *Rickettsia* sp., *Salinibacter* sp., *Salmonella* sp., *Samsonia* sp., *Serratia* sp., *Shigella* sp., *Shimwellia* sp., *Sphingomonas* sp., *Stenotrophomonas* sp., *Thorselliaceae* sp., *Vampirococcus* sp., *Verminephrobacter* sp., *Vibrio* sp., *Victivallis* sp., *Vitreoscilla* sp., *Wolbachia* sp.

Additionally or alternatively, in some embodiments, the fungal infection is caused by a fungus selected from the group consisting of *Aspergillus* sp., *Aureobasidium* sp., *Candida* sp., *Cladosporium* sp., *Curvularia* sp., *Engodontium* sp., *Epicoccum* sp., *Gibberella* sp., *Hypocreales* sp., *Leptosphaerulina* sp., *Malessezia* sp., *Penicillium* sp., *Rhodosporidium* sp., *Trichosporon* sp., *Trichtophyton* sp., and *Ulocladium* sp.

In one aspect, the present disclosure provides a method of protecting a wound from infection in a subject in need thereof, wherein the method comprises administering to the wound a wound dressing composition of any embodiment described herein. Additionally or alternatively, in some embodiments, the wound may be an acute wound or a chronic wound. Additionally or alternatively, in some embodiments, the wound is an acute wound selected from the group consisting of surgical wounds, trauma wounds, donor sites, graft sites, and burn wounds. Additionally or alternatively, in some embodiments, the wound is a chronic wound selected from the group consisting of infectious wounds, venous ulcers, decubitis ulcers and diabetic ulcers. The infection may be a bacterial infection or a fungal infection. In some embodiments, the bacterial infection is caused by gram-negative or gram-positive bacteria.

Examples of gram-positive bacteria include, but are not limited to *Actinomyces* sp., *Arcanobacterium* sp., *Bacillus* sp., *Bavariicoccus* sp., *Brachybacterium* sp., *Clostridium* sp., *Cnuibacter* sp., *Corynebacterium* sp., *Enterococcus* sp., *Desulfitobacterium* sp., *Fervidobacterium* sp., *Georgenia* sp., *Janibacter* sp., *Lactobacillales* sp., *Microbispora* sp., *Nocardia* sp., *Pasteuria* sp., *Pilibacter* sp., *Propionibacterium* sp., *Rathayibacter* sp., *Rhodococcus* sp., *Roseburia* sp., *Rothia* sp., *Sarcina* sp., *Solibacillus* sp., *Sporosarcina* sp., *Staphylococcus* sp., *Streptococcus* sp., *Syntrophomonas* sp., or *Tepidibacter* sp.

Examples of gram-negative bacteria include, but are not limited to *Acetobacter* sp., *Acidaminococcus* sp., *Acinetobacter* sp., *Agrobacterium* sp., *Akkermansia* sp., *Anaerobiospirillum* sp., *Anaerolinea* sp., *Arcobacter* sp., *Armatimonas* sp., *Azotobacter* sp., *Bacteroides* sp., *Bacteroidetes* sp., *Bartonella* sp., *Bdellovibriosp.*, *Brachyspira* sp., *Bradyrhizobium* sp., *Caldilinea* sp., *Cardiobacterium* sp., *Christensenella* sp., *Chthonomonas* sp., *Coxiella* sp., *Cyanobacteria* sp., *Cytophaga* sp., *Dehalogenimonas* sp., *Desulfurobacterium* sp., *Devosia* sp., *Dialister* sp., *Dictyoglomus* sp., *Dinoroseobacter* sp., *Enterobacter* sp., *Escherichia* sp., *Fimbriimonas* sp., *Flavobacterium* sp., *Francisella* sp., *Fusobacterium* sp., *Gluconacetobacter* sp., *Haemophilus* sp., *Helicobacter* sp., *Kingella* sp., *Klebsiella* sp., *Kluyvera* sp., *Kozakia* sp., *Legionella* sp. *Leptonema* sp. *Leptotrichia* sp., *Levilinea* sp. *Luteimonas* sp. *Megamonas* sp., *Megasphaera* sp., *Meiothermus* sp., *Methylobacterium* sp., *Moraxella* sp., *Morganella* sp., *Mycoplasma* sp., *Neisseria* sp., *Nitrosomonas* sp., *Pectinatus* sp., *Pedobacter* sp., *Pelosinus* sp., *Propionispora* sp., *Proteus* sp., *Pseudomonas* sp., *Pseudoxanthomonas* sp., *Rickettsia* sp., *Salinibacter* sp., *Salmonella* sp., *Samsonia* sp., *Serratia* sp., *Shigella* sp., *Shimwellia* sp., *Sphingomonas* sp., *Stenotrophomonas* sp., *Thorselliaceae* sp., *Vampirococcus* sp., *Verminephrobacter* sp., *Vibrio* sp., *Victivallis* sp., *Vitreoscilla* sp., *Wolbachia* sp.

Additionally or alternatively, in some embodiments, the fungal infection is caused by a fungus selected from the group consisting of *Aspergillus* sp., *Aureobasidium* sp., *Candida* sp., *Cladosporium* sp., *Curvularia* sp., *Engodontium* sp., *Epicoccum* sp., *Gibberella* sp., *Hypocreales* sp., *Leptosphaerulina* sp., *Malessezia* sp., *Penicillium* sp., *Rhodosporidium* sp., *Trichosporon* sp., *Trichtophyton* sp., and *Ulocladium* sp.

Any method known to those in the art for administering a wound dressing composition to an acute or a chronic wound disclosed herein may be employed. Suitable methods include in vitro or in vivo methods. In vivo methods typically include the administration of one or more wound dressing compositions to a subject in need thereof, suitably a human. When used in vivo for therapy, the one or more wound dressing compositions described herein are administered to the subject in effective amounts (i.e., amounts that have desired therapeutic effect). The dose and dosage regimen will depend upon the state of the wound of the subject, and the characteristics of the particular wound dressing composition used.

The effective amount may be determined during pre-clinical trials and clinical trials by methods familiar to physicians and clinicians. An effective amount of one or more wound dressing compositions useful in the methods may be administered to a subject in need thereof by any number of well-known methods for administering wound dressing compositions.

In some embodiments of the methods of the present technology, the wound dressing compositions are administered daily for 1 hour or more. In some embodiments of the methods of the present technology, the wound dressing compositions are administered daily for 2 hours or more. In some embodiments of the methods of the present technology, the wound dressing compositions are administered daily for 3 hours or more. In some embodiments of the methods of the present technology, the wound dressing compositions are administered daily for 4 hours or more. In some embodiments of the methods of the present technology, the wound dressing compositions are administered daily for 5 hours or more. In some embodiments of the methods of the present technology, the wound dressing compositions are administered daily for 6 hours or more. In some embodiments of the methods of the present technology, the wound dressing compositions are administered daily for 12 hours or more. In some embodiments of the methods of the present technology, the wound dressing compositions are administered daily for 1 week or more. In some embodiments of the methods of the present technology, the wound dressing compositions are administered daily for 2 weeks or more. In some embodiments of the methods of the present technology, the wound dressing compositions are administered daily for 3 weeks or more. In some embodiments of the methods of the present technology, the wound dressing compositions are administered daily for 4 weeks or more. In some embodiments of the methods of the present technology, the wound dressing composition can be changed for a chronic wound as appropriate.

In some embodiments, administration of the wound dressing composition of the present technology results in at least a 1.5-fold, at least a 2-fold, at least a 2.5-fold, at least a 3-fold, at least a 3.5-fold, at least a 4-fold, at least a 4.5-fold, at least a 5-fold, at least a 5.5-fold, at least a 6-fold, at least a 6.5-fold, at least a 7-fold, at least a 7.5-fold, at least an 8-fold, at least an 8.5-fold, at least a 9-fold, at least a 9.5-fold, or at least a 10-fold increase in angiogenesis, vasodilation, or immune response in the subject compared to that observed in the subject prior to administration of the wound dressing composition. Angiogenesis can be monitored over time using a bNIRS (broadband near-infrared spectroscopy) system to monitor total hemoglobin (tHb) as a marker of blood volume (see Yang, R., et al., *J. Biomed. Opt.*, 18:16011(2013)).

Methods of Making the Wound Dressing Composition of the Present Technology

In one aspect, the present disclosure provides a method for making the wound dressing compositions of any embodiment disclosed herein. Additionally or alternatively, in some embodiments, the wound dressing compositions of the present technology comprise a first layer and a second layer, wherein the first layer comprises a collagen and an oxidized cellulose, and wherein the second layer comprises a nitrite source. Additionally or alternatively, in some embodiments, the first layer may comprise a bioresorbable freeze dried sponge and the second layer may comprise a material saturated with a nitrite solution of any nitrite source disclosed herein.

For example, in some embodiments, the bioresorbable freeze dried sponge may comprise a combination of a collagen and an oxidized regenerated cellulose (ORC) in a ratio of about 70 wt. %:30 wt. %, about 65 wt. %:35 wt. %, about 60 wt. %:40 wt. %, about 55 wt. %:45 wt. %, about 50 wt. %:50 wt. %, about 45 wt. %:55 wt. %, about 40 wt. %:60 wt. %, about 35 wt. %:65 wt. %, about 30 wt. %:70 wt. %, or any range including and/or in between any two of these values. Additionally or alternatively, in some embodiments, the bioresorbable freeze dried sponge may comprise a combination of a collagen and an oxidized regenerated cellulose (ORC) in a ratio of about 55 wt. %:45 wt. %.

The bioresorbable freeze dried sponge of the first layer may be produced by adding a collagen (either in paste or powder form) to an acidic solution (e.g., about 0.05 M acetic acid or other soluble organic acids), which may result in a final solution with 0.55 g solid collagen weight per 100 mL acid solution. The collagen will then be blended with the acid solution and allowed to swell to produce a homogenous slurry, at which point the ORC is blended into the collagen slurry (0.45 g ORC per 100 mL slurry) to generate a slurry material with about 1% solid content. Additionally or alternatively, in some embodiments, a slurry material may be generated with a solid content of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, or any range including and/or in between any two of these values. The resulting slurry is then degassed using a vacuum to remove trapped air and dispensed into a container before being flash frozen in a $-70°$ C. freezer to form a block. Additionally or alternatively, in some embodiments, the resulting slurry may be flash frozen in a freezer at a temperature of about $-70°$ C., $-65°$ C., $-60°$ C., $-55°$ C., $-50°$ C., $-45°$ C., $-40°$ C., $-35°$ C., $-30°$ C., $-25°$ C., $-20°$ C., or any range including and/or in between any two of these values. The resulting block of collagen/ORC may then freeze dried to produce a bioresorbable sponge material.

In some embodiments, the saturated material of the second layer may comprise a material selected from the group consisting of gauze, cotton, rayon, polyester, collagen, gelatin, chitosan, fibronectin, hyaluronic acid, polysaccharides, a coating, a gel, a liquid, and any combination thereof. Additionally or alternatively, in some embodiments, the saturated material of the second layer may be saturated in any nitrite source disclosed herein. In some embodiments, the saturated material of the second layer is a gauze. The saturated material of the second layer may be equivalent or smaller in size than the freeze dried bioresorbable sponge material of the first layer. The saturated materials of the second layer typically have a low absorbency, and consequently are quickly saturated in solution (e.g., any nitrite solution disclosed herein). The material of the second layer may immersed in a saturated nitrite solution of any nitrite source disclosed herein for about 10 seconds, about 20 seconds, about 30 seconds, about 40 seconds, about 50 seconds, about 1 minute, about 2 minutes, about 3 minutes, about 4 minutes, about 5 minutes, about 6 minutes, about 7 minutes, about 8 minutes, about 9 minutes, about 10 minutes, or any range including and/or in between any two of these values, to saturate the material with the nitrite solution. Additionally or alternatively, in some embodiments, the material may be immersed in a saturated nitrite solution of any nitrite source disclosed herein for about 1 minute. Additionally or alternatively, in some embodiments, the material of the second layer may be stored in a sealed pouch with the saturated nitrite solution of any nitrite source disclosed herein until applied to a wound bed, after being pre-saturated with a saturated nitrite solution of any nitrite source disclosed herein. Additionally or alternatively, in some embodiments, the material of the second layer may be stored in a sealed pouch with the saturated nitrite solution of any nitrite source disclosed herein until applied to a wound bed, before being pre-saturated with a saturated nitrite solution of any nitrite source disclosed herein.

The first layer and the second layer of the wound dressing composition are combined upon application into the wound bed. The two layers may not be adhered or bonded together. The saturated material of the second layer may be placed directly onto the wound bed and the first layer (e.g., freeze dried bioresorbable sponge of the first layer) may be placed directly over it. The proximity of the the two layers, and their subsequent interaction, may generate the nitric oxide in the wound bed as the freeze dried bioresorbable sponge of the first layer contacts fluid (nitrite solution and/or wound fluid) causing the first layer to gel, coating the saturated material of the second layer.

Kits Comprising the Wound Dressing Composition of the Present Technology

In a further related aspect, the present disclosure provides kits that include a wound dressing composition of any embodiment described herein and instructions for use. The kit may optionally include instructions for generating a wound dressing composition of any embodiment described herein. The kits of the present technology may also include methods for treating a wound in a subject in need thereof. The kit may optionally comprise components such as antiseptic wipes, ointment, adhesive tape, tweezers, or scissors.

EXAMPLES

The present technology is further illustrated by the following Example, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

Example 1: Increased Nitric Oxide Production With Bilayer Wound Dressing Composition A zone of inhibition (ZOI) assay was utilized to assess the antimicrobial effect of collagen/ORC in combination with a nitrite source by measuring nitric oxide production of the wound dressing compositions (FIG. 1).

Briefly, agar plates (tryptone soy agar) were inoculated with either a gram-negative (*P. aeruginosa*) or gram-positive (*S. aureus*) bacteria through the addition of 0.1 mL of bacterial suspension (~$2.0 \times 10^8$ CFU/mL) to each plate. Once applied to the agar plate the bacterial suspension was evenly spread and allowed to air dry. The inoculated plates were incubated for 1 hour at 37° C. Following incubation, the bilayer dressing sample (collagen/ORG dressing+gauze soaked with sodium nitrite), the first layer alone (collagen/ORC dressing), or the second layer alone (gauze soaked with sodium nitrite) were then applied centrally to the agar plates and were incubated for 24 hours at 37° C. to permit bacterial growth. Following incubation, the samples were assessed for a zone of inhibition (area around the dressing devoid of bacterial growth). Where a zone of inhibition was observed, this was measured by assessing the average distance between the sample and the edge of the visible bacterial growth. Samples were tested in triplicate for each bacterial strain FIG. 1 demonstrates that the second layer alone had no antimicrobial effect on either gram-negative or gram-positive bacteria. Significant bacterial growth was observed on the second layer alone. The collagen/ORC layer alone also exhibited minimal antimicrobial activity, with a ZOI of 0 mm for *P. aeruginosa* and 0.2 mm for *S. aureus* (FIG. 1). In contrast, the ZOI observed with the bilayer wound dressing composition was 2.3 mm and 1.5 mm for *P. aeruginosa* and *S. aureus*, respectively. These results demonstrate that the antimicrobial effects of the bilayer wound dressing composition, comprising the first layer and the second layer, demonstrated was significantly higher compared to that of the individual layers.

To further assess the antibacterial potency of the wound dressing compositions of the present technology, a swab analysis was also conducted after completion of the ZOI assay. Briefly, following the removal of each dressing sample from the ZOI assay described above, the area directly beneath the dressing was swabbed using a sterile swab and streaked out onto a fresh agar plate (FIG. 2). These agar plates were then incubated for 24 hours at 37° C. Following incubation, the agar plates were assessed for levels of bacterial growth. Bacterial growth was significantly reduced for the bilayer wound dressing composition compared to that observed with the collagen/ORC layer alone.

These results demonstrate that the bilayer wound dressing composition of the present technology exhibits a greater antimicrobial effect compared to collagen/ORC alone, and that the bilayer wound dressing composition disclosed herein is effective in promoting nitric oxide production. Accordingly, the wound dressing compositions of the present technology are useful in methods for treating infected wounds and/or protecting wounds from infection in a subject in need thereof.

Example 2: Manufacture of the Wounds Dressing Compositions of the Present Technology The wound dressing compositions of the present technology may comprise a first layer and a second layer, wherein the first layer comprises a collagen and an oxidized cellulose, and wherein the second layer comprises a nitrite source. In a non-limiting example, the first layer comprises a bioresorbable freeze dried sponge and the second layer comprises a material saturated with a solution of sodium nitrite. The bioresorbable freeze dried sponge of the first layer comprises a combination of a collagen and an oxidized regenerated cellulose (ORC) at a ratio of 55 wt. %:45 wt. %. The bioresorbable freeze dried sponge of the first layer will be produced by adding a collagen (either in paste or powder form) to an acidic solution (e.g., 0.05 M acetic acid or other soluble organic acids), resulting in a final solution with 0.55 g solid collagen weight per 100 mL acid solution. The collagen will be blended with the acid solution and will be allowed to swell to produce a homogenous slurry, at which point the ORC will be blended into the collagen slurry (e.g., 0.45 g ORC per 100 mL slurry) to generate a slurry material with approximately 1% solid content. The resulting slurry will then be degassed using a vacuum to remove trapped air, dispensed into a container, and flash frozen in at −70° C. in a freezer to form a block. The resulting block of collagen/ORC will then be freeze dried to produce the bioresorbable sponge material of the first layer.

The saturated material of the second layer may be any medically acceptable material, such as gauze, cotton, rayon, polyester, collagen, gelatin, chitosan, fibronectin, hyaluronic acid, polysaccharides, a coating, a gel, a liquid, or any combination thereof. The saturated material of the second layer will be equivalent or smaller in size than the freeze dried bioresorbable sponge material of the first layer. The saturated materials of the second layer typically have a low absorbency, and consequently are quickly saturated in solution (e.g. any nitrite solution disclosed herein). The material of the second layer will be immersed in a solution of saturated sodium nitrite for 1 minute to saturate the material with the sodium nitrite.

The first layer and the second layer of the wound dressing composition will be combined upon application into the wound bed, however, the two layers may not be adhered or bonded together. The saturated material of the second layer will be placed directly onto the wound bed and the first layer (e.g., the freeze dried bioresorbable sponge of the first layer) will be placed directly over it. The proximity of the the two layers, and their subsequent interaction, will generate the nitric oxide in the wound bed as the freeze dried bioresorbable sponge of the first layer contacts fluid (nitrite solution and/or wound fluid) which will cause the first layer to gel and thus coat the saturated material of the second layer.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A wound dressing composition comprising a first layer and a second layer, wherein the first layer comprises a collagen and an oxidized cellulose, and wherein the second layer comprises a nitrite source, optionally wherein the collagen is selected from the group consisting of a mammalian collagen, a marine collagen, a porcine collagen, a bovine collagen, an ovine collagen, an equine collagen, a mammalian recombinant collagen, a human recombinant collagen and any combination thereof.

2. The wound dressing composition of claim 1, wherein the human recombinant collagen is a mixture of type I human recombinant collagen and type III human recombinant collagen, or
    wherein the bovine collagen is a mixture of type I bovine collagen and type III bovine collagen, optionally wherein the ratio by weight of type I bovine collagen to type III bovine collagen is about 85:15.

3. The wound dressing composition of claim 2, wherein the type I human recombinant collagen is human recombinant collagen type I, alpha I or human recombinant collagen type I, alpha II, or
    wherein the type III human recombinant collagen is human recombinant collagen type III, alpha I, or
    wherein the ratio by weight of type I human recombinant collagen to type III human recombinant collagen is greater than 70:30.

4. The wound dressing composition of claim 1, wherein the oxidized cellulose comprises oxidized regenerated cellulose (ORC) or wherein the oxidized cellulose of the first layer comprises fiber lengths of about 5 μm to about 1,000 μm.

5. The wound dressing composition of claim 1, wherein the first layer comprises
    about 30 wt. % to about 95 wt. % of collagen, with a weight-average molecular weight of about 5,000 to about 100,000, or
    about 30 wt. % to about 70 wt. % of oxidized cellulose, with a weight-average molecular weight of about 50,000 to about 1,000,000, or
    a freeze dried sponge or a film, or
    one or more additional biomaterials selected from the group consisting of gelatin, chitosan, fibronectin, hyaluronic acid, polysaccharides, and any combination thereof, or
    at least one antimicrobial agent selected from the group consisting of tetracycline, penicillins, terramycins, erythromycin, bacitracin, neomycin, polymycin B, mupirocin, clindamycin, colloidal silver, silver salts, silver sulfadiazine, chlorhexidine, povidone iodine, triclosan, sucralfate, quaternary ammonium salts, and any combination thereof, or at least one antioxidant selected from the group consisting of anthocyanins, astaxanthin, bilirubin, canthaxanthin, capsaicin, citric acid, curcumin, coenzyme Q10, eugenol, flavanol, flavonolignans, flavanone, flavone, flavonol, iodide, isoflavone phytoestrogen, lutein, lycopene, manganese, melatonin, N-acetylcysteine, oxalic acid, phenolic acid, phytic acid, R-α-lipoic acid, stilbenoid, tocopherol, tocotrienol, vitamin A, vitamin C, vitamin E, xanthones, zeaxanthin, α-carotene, β-carotene, and any combination thereof, or at least one signaling protein selected from the group consisting of PDGF, TGFβ, FGF, EGF, and any combination thereof.

6. The wound dressing composition of claim 1 wherein the wound dressing composition is a single multi-layered dressing, wherein the first layer and the second layer are adjoined.

7. The wound dressing composition of claim 5, wherein the anthocyanins are selected from the group consisting of cyanidin, delphinidin, malvidin, pelargonidin, peonidin, petunidin, and any combination thereof, or wherein the flavanol is catechin, epicatechin, theaflavin, thearubigins, gallocatechin, epigallocatechin, or any gallate ester thereof, or any combination thereof, or wherein the flavanone is eriodictyol, hesperetin, naringenin, or any combination thereof, or wherein the flavone is apigenin, luteolin, tangeritin, or any combination thereof, or wherein the flavonol is isorhamnetin, kaempferol, myricetin, proanthocyanidins, quercetin, rutin, or any combination thereof, or wherein the isoflavone phytoestrogen is daidzein, genistein, glycitein, or any combination thereof, or wherein the phenolic acid is chicoric acid, chlorogenic acid, cinnamic acid, ellagic acid, ellagitannins, gallic acid, gallotannins, rosmarinic acid, salicylic acid, or any ester thereof, or any combination thereof, or wherein the stilbenoid is resveratrol, pterostilbene, or any combination thereof.

8. The wound dressing composition of claim 1, wherein the nitrite source is selected from the group consisting of aluminum nitrite, ammonium nitrite, cadmium nitrite, chromium (II) nitrite, chromium (III) nitrite, cobalt (II) nitrite, cobalt (III) nitrite, copper (I) nitrite, copper (II) nitrite, gallium (III) nitrite, iron (II) nitrite, iron (III) nitrite, lead (II) nitrite, lead (IV) nitrite, silver nitrite, tin (II) nitrite, tin (IV) nitrite, zinc nitrite, and any combination thereof.

9. The wound dressing composition of claim 1 any one of claims 1-8, wherein the second layer comprises about 1 wt. % to about 90 wt. % of the nitrite source.

10. The wound dressing composition of claim 1, wherein the secondlayer comprises a bioresorbable layer, optionally wherein the bioresorbable layer comprises about 5 wt. % to about 100 wt. % of the second layer or wherein the bioresorbable layer is selected from the group consisting of collagen, gelatin, chitosan, fibronectin, hyaluronic acid, polysaccharides, and any combination thereof.

11. The wound dressing composition of claim 1, wherein the second layer comprises a non-bioresorbable layer, optionally wherein the non-bioresorbable layer comprises about 10 wt. % to about 99 wt. % of the second layer or wherein the non-bioresorbable layer is selected from the group consisting of a coating, a gel, a liquid, and any combination thereof.

12. A method for protecting a wound from infection or treating a wound in a subject in need thereof, comprising administering to the wound a wound dressing composition comprising a first layer and a second layer, wherein the first layer comprises an effective amount of a collagen and an oxidized cellulose, and wherein the second layer comprises an effective amount of a nitrite source.

13. The method of claim 12, wherein the first layer and the second layer are adjoined.

14. The method of claim 12, wherein the first layer and the second layer are not adjoined.

15. The method of claim 12, wherein the wound dressing composition induces, enhances, or promotes at least of one angiogenesis, vasodilation, or immune response in the subject.

16. The method of claim 12, wherein the wound dressing composition is bioresorbable and is administered directly to the wound.

17. The method of claim 12, wherein the wound dressing composition is non-bioresorbable and is administered directly to the wound.

18. A method for making a wound dressing comprising:
providing a first layer comprising an effective amount of a collagen and an oxidized cellulose;
providing a second layer comprising an effective amount of a nitrite source; and
combining the first layer and the second layer to form the wound dressing.

19. A kit comprising the wound dressing composition of claim 1 and instructions for use.

* * * * *